United States Patent [19]

Tacklind et al.

[11] Patent Number: 5,342,304
[45] Date of Patent: Aug. 30, 1994

[54] INFLATION DEVICE FOR DILATATION CATHETERS

[75] Inventors: Christopher A. Tacklind; Vae E. Sun, both of Palo Alto; Nelson S. Au, Foster City, all of Calif.

[73] Assignee: Advanced Cardiovascular Systems, Inc., Santa Clara, Calif.

[21] Appl. No.: 134,872

[22] Filed: Oct. 12, 1993

Related U.S. Application Data

[63] Continuation of Ser. No. 742,215, Aug. 6, 1991, abandoned, which is a continuation of Ser. No. 494,734, Mar. 16, 1990, abandoned.

[51] Int. Cl.$^5$ ............................................. A61M 29/00
[52] U.S. Cl. ......................................... 604/99; 604/211
[58] Field of Search ................ 604/99, 100, 186, 187, 604/206–211; 222/287, 391

[56] References Cited

U.S. PATENT DOCUMENTS

| | | |
|---|---|---|
| B14,323,071 | 5/1990 | Simpson et al. . |
| 4,332,254 | 6/1982 | Lundquist . |
| 4,439,185 | 3/1984 | Lundquist .............................. 604/97 |
| 4,468,224 | 8/1984 | Enzmann et al. ..................... 604/247 |
| 4,516,972 | 5/1985 | Sampson ............................... 604/282 |
| 4,538,622 | 9/1985 | Sampson et al. . |
| 4,554,929 | 11/1985 | Sampson et al. . |
| 4,569,347 | 2/1986 | Frisbie . |
| 4,571,240 | 2/1986 | Sampson et al. . |
| 4,583,974 | 4/1986 | Kokernak et al. . |
| 4,638,805 | 1/1987 | Powell . |
| 4,655,749 | 4/1987 | Fischione et al. . |
| 4,743,230 | 5/1988 | Nordquest ............................ 604/97 |
| 4,832,692 | 5/1989 | Box et al. . |
| 4,865,591 | 9/1989 | Sams .................................... 604/208 X |
| 4,919,121 | 4/1990 | Rydell et al. . |
| 4,929,238 | 5/1990 | Baum ................................... 604/208 |
| 4,973,318 | 11/1990 | Holm et al. ........................... 604/211 X |

*Primary Examiner*—John D. Yasko
*Attorney, Agent, or Firm*—Crosby, Heafey, Roach & May

[57] ABSTRACT

An apparatus for inflating and deflating a balloon on a dilatation catheter in order to perform an angioplasty procedure therewith. The inflation/deflation apparatus has an elongated housing with a piston disposed within a bore within the housing and a threaded piston rod connected to the piston. A threaded split collar or nut is disposed about and engaged with the threaded piston which allows the piston rod to be rotated about its axis in order to move the piston longitudinally in small increments within the bore of the housing. Flexible arms are connected to each half of the split collar or nut which when moved away from the piston rod, disengage the split collar or nut from the piston rod and allow longitudinal movement of the piston within the bore by pushing on the piston rod.

17 Claims, 5 Drawing Sheets

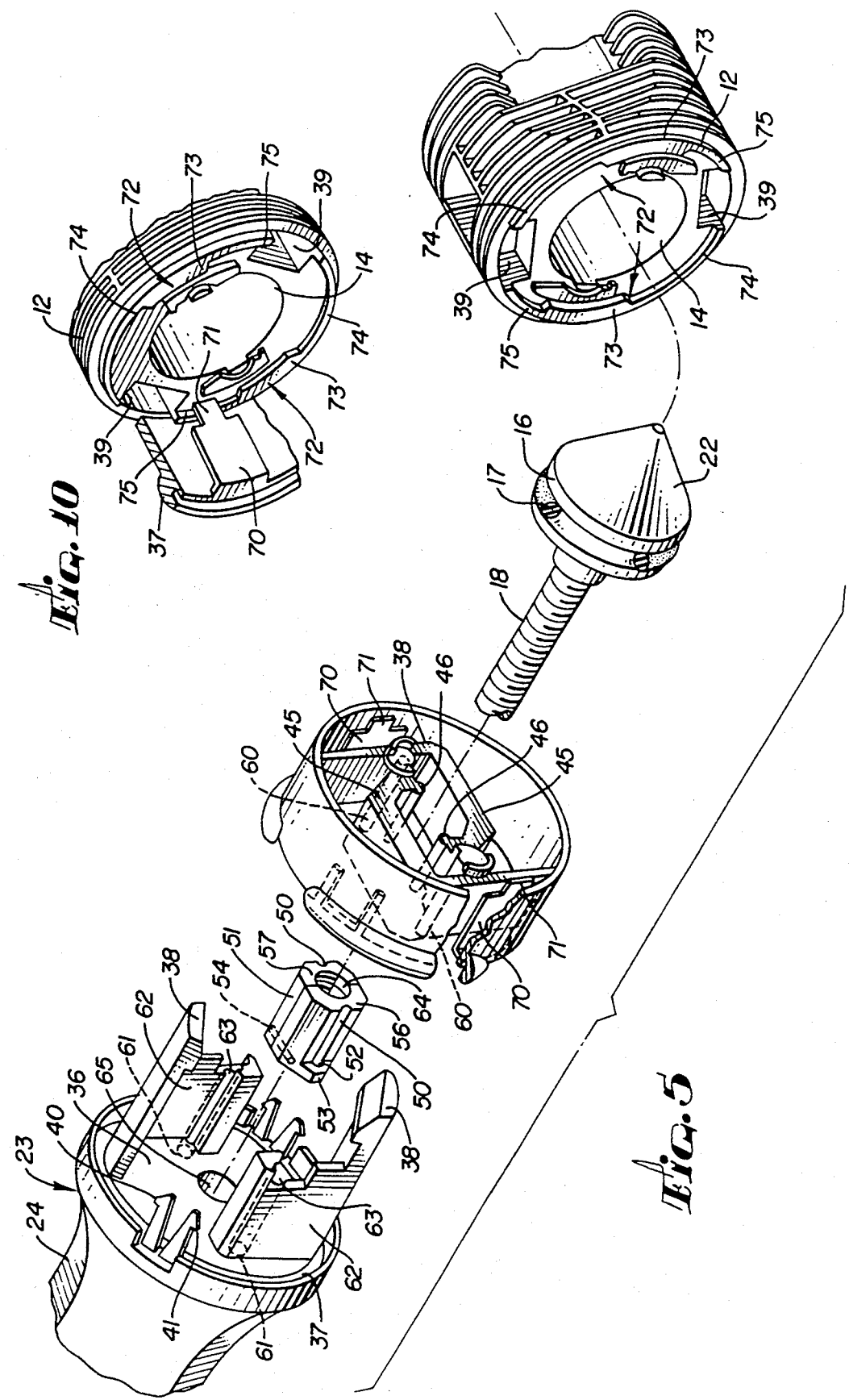

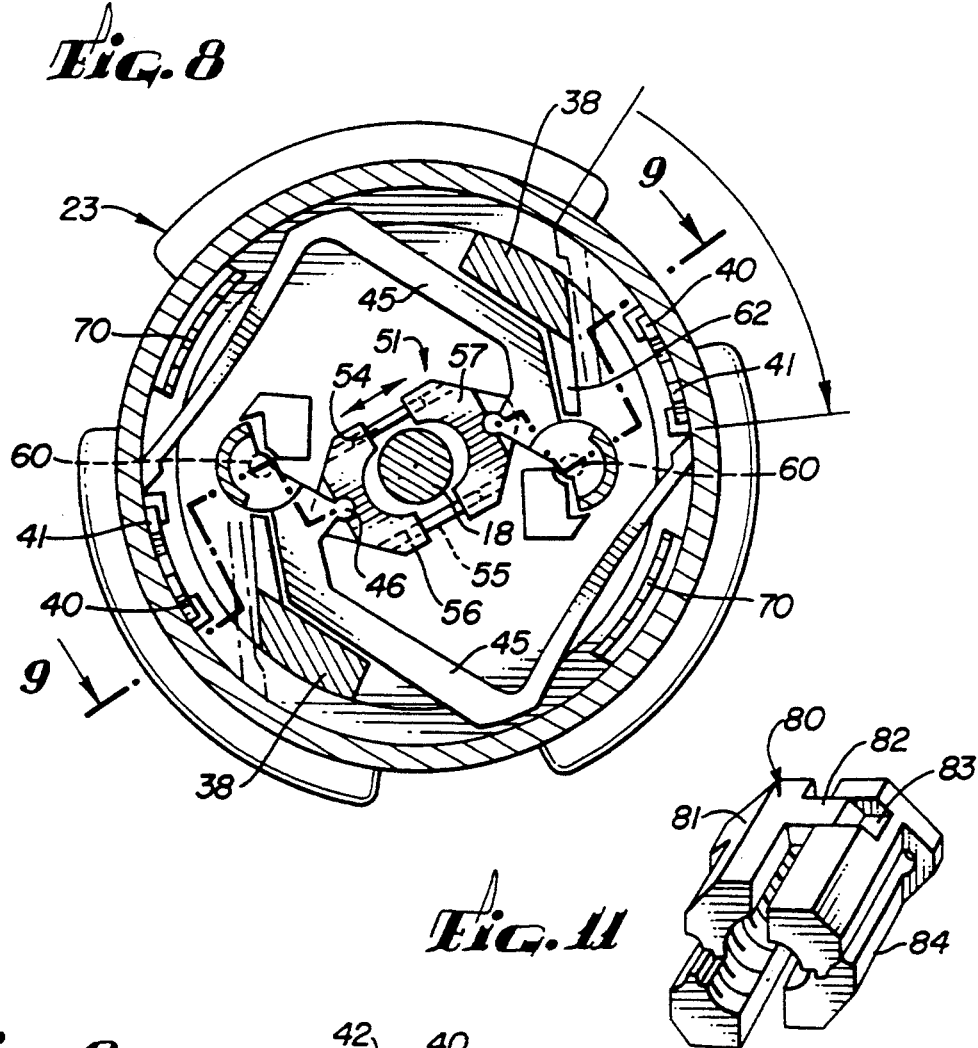
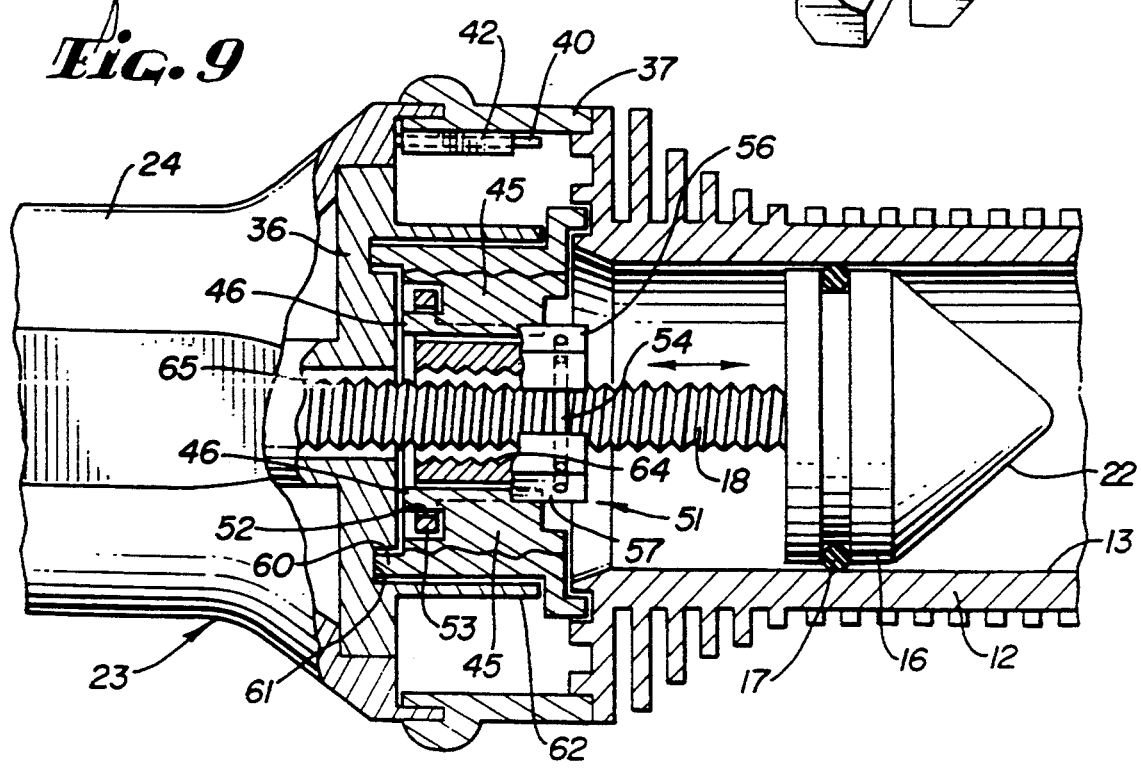

INFLATION DEVICE FOR DILATATION CATHETERS

This is a continuation of copending application Ser. No. 07/742,215 which was filed on Aug. 6, 1991. Now abandoned, which is a continuation of Ser. No. 07/494,734 filed Mar. 16, 1990 now abandoned.

BACKGROUND OF THE INVENTION

This invention generally relates to angioplasty procedures such as percutaneous transluminal coronary angioplasty (PTCA) and particularly to inflation/deflation devices for use in such procedures.

In PTCA procedures, a dilatation catheter having an inflatable, relatively inelastic balloon on the distal end thereof is advanced through a patient's arterial system until the balloon crosses the atherosclerotic lesion to be dilated. The balloon is inflated to a predetermined size with radiopaque liquid by syringe-like inflation device mounted on the proximal end of the dilatation catheter to dilate the lesion and then deflated so that the catheter can be removed from the stenotic region and blood flow resumed.

The first step of the procedure is to percutaneously introduce a guiding catheter having a preformed distal tip into the patient's arterial system (e.g. the femoral artery) and advance the catheter therein until preformed distal tip thereof is seated within the ostium of the appropriate coronary artery. A guidewire is preloaded within an inner lumen of the dilatation catheter and both are then advanced through the previously positioned guiding catheter to the distal end thereof. The guidewire is first advanced out of the distal tip of the guiding catheter into the patient's coronary artery until the distal end of the guidewire crosses the stenotic arterial region to be dilated. The dilatation catheter is then advanced out of the guiding catheter over the guidewire until the inflatable balloon on the distal end thereof is positioned across the stenosis. The balloon is inflated with radiopaque liquid to a relatively high pressure (e.g. up to 8 atmospheres or more) by the inflation device to dilate the stenosis. After the dilatation, the balloon is deflated and the catheter removed.

For a more detailed description of the procedures and the devices used in such procedures, reference is made to U.S. Pat. No. 4,332,254 (Lundquist), U.S. Pat. No. 4,323,071 (Simpson-Robert), U.S. Pat. No. 4,439,185 (Lundquist), U.S. Pat. No. 4,468,224 (Enzmann, et.al.), U.S. Pat. No. 4,516,972 (Samson), U.S. Pat. No. 4,538,622 (Samson, et.al.), U.S. Pat. No. 4,554,929 (Samson, et.al.), U.S. Pat. No. 4,569,347 (Frisbie), U.S. Pat. No. 4,571,240 (Samson, et.al.), U.S. Pat. No. 4,638,805 (Powell), and U.S. Pat. No. 4,743,230 (Nordquest), each of which are hereby incorporated herein in their entirety by reference thereto.

The use of the various devices in angioplasty procedures requires a fair degree of manual dexterity on the part of the physician performing the procedures and frequently one or more assistants are also required. The inflation and deflation of the balloon on the dilatation catheter for priming the catheter and venting air therefrom and for performing the dilatation can be particularly demanding.

Most commercially available inflation devices for angioplasty catheters are essentially syringes with pressure gauges attached thereto. They generally have two modes of operation. In one mode, the piston and attached piston rod of the syringe are free to move longitudinally within the inner bore of the syringe by pulling on a handle provided on the piston rod to pull a vacuum so as to draw inflation fluid into the bore of the syringe or by pushing on the handle to discharge such inflation fluid out the end of the syringe. In the other mode, the piston rod, which is threaded, is engaged with an element of the device so that the longitudinal movement within the bore is effected by rotation of the piston rod. For a more detailed description of such inflation devices reference is made to U.S. Pat. No. 4,743,230 which has been incorporated herein by reference. While these inflation devices have been effective for their intended uses, they have not always been very convenient for the physician to use particularly when changing from one mode of operation to another. Additionally, they could not always maintain a locked position under high pressure.

What has been needed and heretofore unavailable is an inflation device which is easy for the physician to use, particularly when changing the modes of operation. The present invention satisfies this need.

SUMMARY OF THE INVENTION

The present invention is directed to an improved inflation/deflation device for balloon dilatation catheters which are employed in angioplasty procedures, particularly coronary angioplasty procedures.

An inflation device in accordance with the present invention includes an elongated housing with opposed ends, one of which is open and one which is essentially closed except for a small-diameter conduit extending therethrough, and an inner bore extending therebetween. A piston with a sealing member around the circumference thereof is slidably disposed within the inner bore of the housing and has a piston rod secured thereto which extends out of the open end of the housing. At least a portion of the piston rod has threads on the exterior thereof and a handle is provided on the end which extends out of the housing.

A plurality of opposed threaded members, such as a split collar or nut with a threaded passageway therethrough, is provided with a positioning means connected thereto to engage the threaded exterior portion of the piston rod in a first position and to disengage the opposed threaded members from the piston rod in a second position. The first position allows the inflation device to be operated by rotating the piston rod to move the piston longitudinally within the bore and the second position allows the inflation device to be operated by pushing and pulling on the piston rod to move the piston longitudinally within the bore.

In a preferred embodiment of the invention, the positioning means is connected to a rotatable sleeve mounted on the end of the housing through which the piston rod extends and coaxial therewith can be operated by the fingers of the operator's hand engaging the handle notwithstanding the position of the handle. Axial rotation of the sleeve in one direction to the first position moves the opposed threaded member into engagement with the threaded portion of the piston rod and axial rotation of the sleeve in a second direction opposite the first to a second position disengages the opposed threaded member therefrom. The positioning means includes a two position switch which has little or no dead band between the two positions, i.e. the switch snaps into position to avoid the mispositioning thereof.

The conduit extending from the tapered end of the bore is in fluid communication with a flexible, elongated tubular member secured to the housing. A pressure gauge, preferably with a pressure display means, is provided in fluid communication with the conduit extending from the tapered end of the bore so that fluid pressure can be readily monitored when using the inflation device. A valve is preferably provided on the end of the flexible, elongated tubular member so that inflation liquid can be withdrawn from a container containing same into the inner bore of the housing in a first valve position and the withdrawn inflation fluid can be injected into and withdrawn from the proximal end of a dilatation catheter in a second position. Preferably a third position is provided to close off all fluid flow through the tubular member.

The inflation device of the invention greatly simplifies the inflation and deflation of angioplasty catheters and provides a greater degree of safety than prior devices. These and other advantages of the invention will become more apparent from the following detailed description thereof when taken in conjunction with the accompanying exemplary drawing.

BRIEF DESCRIPTION OF THE DRAWINGS

FIG. 5 is a partial exploded perspective view of the inflation device illustrating the inner relationship of the components thereof, with the components in a first position;

FIG. 8 is a transverse cross-sectional view as in FIG. 6 with the components in a second position;

FIG. 9 is a longitudinal view taken along the lines of 9—9 shown in FIG. 8;

FIG. 10 is a partial, cut away perspective view of portions of the inflation device shown on FIG. 1; and FIG. 11 is a perspective of an alternate embodiment of a split-nut useful in the inflation device of the invention.

DETAILED DESCRIPTION OF THE INVENTION

Figure 1:
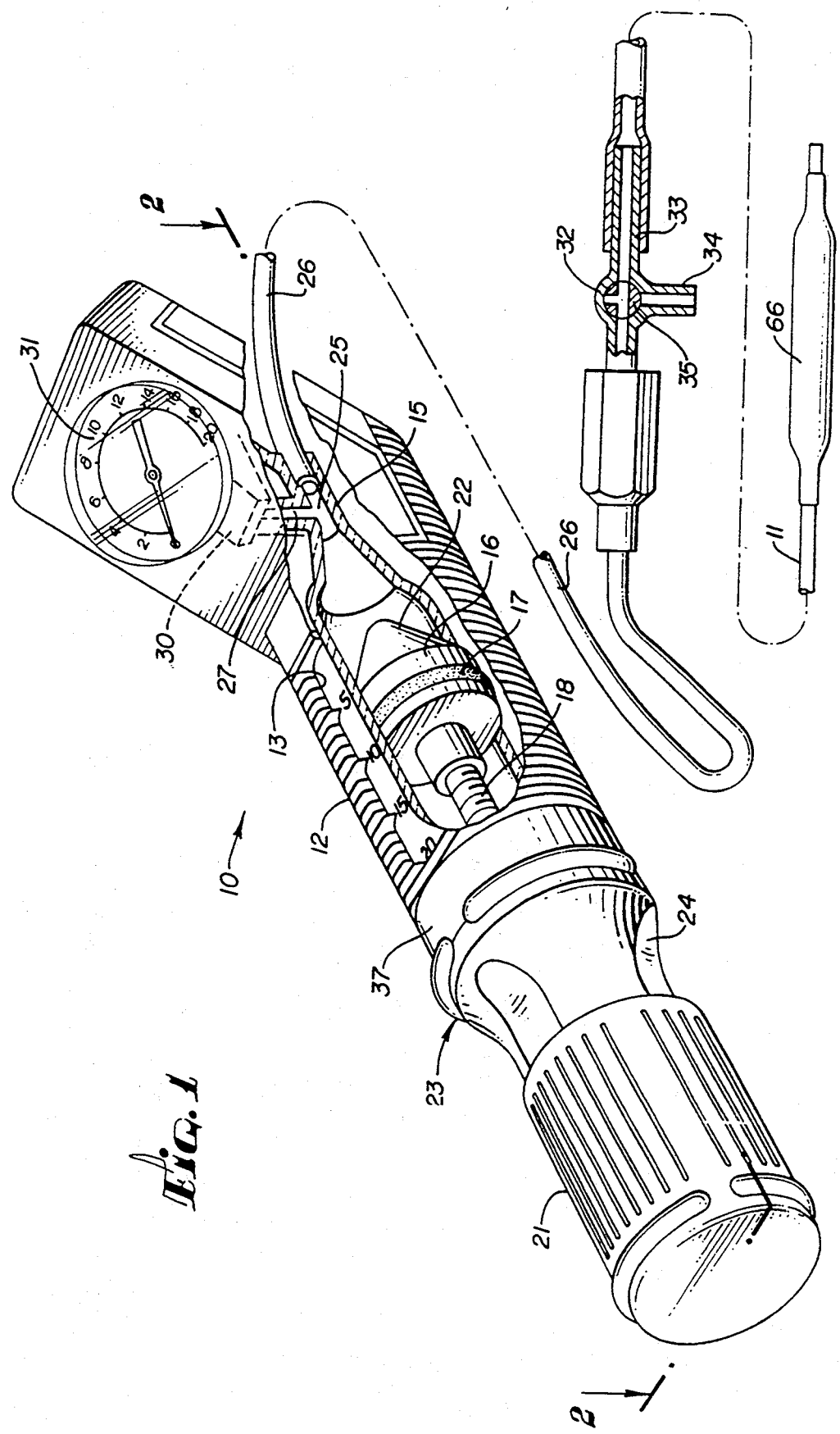
FIG. 1 is a perspective view, partially in section, of an inflation device embodying features of the invention which is connected to the proximal end of a balloon dilatation catheter.
Figure 2:
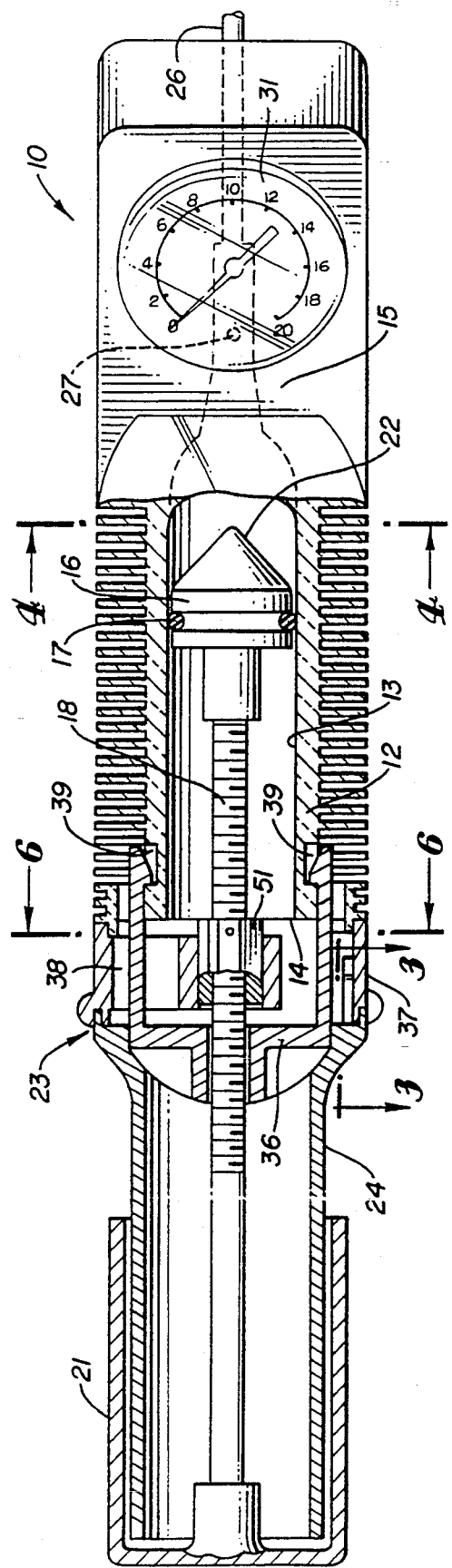
FIG. 2 is a plan view, partially in section, of an inflation device shown in FIG. 1 taken along the lines 2—2 shown in FIG. 1 and 6.
Figure 4:
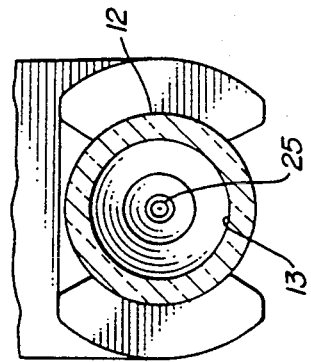
FIG. 4 is a transverse cross-sectional view taken along the lines of 4—4 shown in FIG. 2.

Reference is made to FIG. 1 which illustrates an inflation device 10 embodying features of the invention connected to the proximal end of a balloon dilatation catheter 11 and also to FIGS. 2 and 5 which illustrate interior details of the device. The inflation device 10 generally includes an elongated housing 12 with an inner bore 13 extending between open-end 14 and an opposing essentially closed end 15. A piston 16 with a sealing ring 17 of rubber, elastic or other suitable material disposed around the circumference thereof is slidably disposed within the inner bore 13. A piston rod 18 is secured by one end thereof to the rear of piston 16 and the free end thereof extends out the open end of the housing 12 and is provided with a handle 21 to facilitate moving the piston 16 within the inner bore 13. The front or pressure side 22 of piston 16 is provided with a taper which matches or closely matches the taper provided in the essentially closed end 15 of the housing 12. An operation mode selector switch 23 is located at the open end 14 of the housing 12 and is provided with an extension member 24 to facilitate its use by the physician while holding the handle 21.

A relatively short conduit 25 extends through essentially closed end 15 of the housing 12 and connects in fluid communication tubular member 26 with the inner bore 13. A three way valve 32 is secured to the distal end of tubular member 26 and has one outlet 33 which connects the tubular member 26 in fluid communication with the proximal end of dilatation catheter 11 and another outlet 34 which connects the tubular member in fluid communication with a container (not shown) of inflation fluid. A valve body 35 is rotated by a handle (not shown) in the valve 32 to select three positions, one position connecting outlet 33 with tubular member 26, a second position connecting outlet 34 with tubular member 26 and a third position closing the two outlets. The first position is shown in FIG. 1.

A short, side conduit 27 connects the conduit 25 with pressure sensor 30 which has a pressure display 31 associated therewith. While the embodiment shown utilizes conventional mechanical linkages (not shown) between the pressure sensor and the pressure display, an electrical or electronic pressure sensor with an analog or digital display would be suitable.

Figure 3:
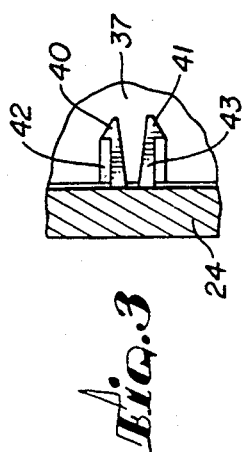
FIG. 3 is a cross-sectional view taken along the lines of 3—3 shown in FIG. 2.

The details of the operation mode selector switch 23 are best shown in FIGS. 2 and 5 and generally include a base 36 fixed to the open end 14 of the housing 12 by means of fingers 38 which project therefrom and which interfit recesses 39 provided in the housing 12. A selector sleeve 37 is rotatably mounted onto the open end 14 of housing 12. Extension 24 is secured to the sleeve 37 by two pairs of fingers 40 and 41 which interfit ridges 42 and 43 as shown in FIG. 3.

The switching mechanism 38 has a pair of angular spring elements, such as L-shaped arms 45 which are fixed at one end thereof to the interior of the selector sleeve 37. Each of the arms 45 has a post 46 adjacent the free end thereof with an extension 47, which during assembly slides along the groove 50 on the exterior of the split collar or nut 51 until the extension 47 thereon seats within aperture or opening 52 provided in flange 53. A pair of guidepins 54 and 55 disposed within passageways provided in the split-nut 51 guide the movement of the split-nut halves 56 and 57 toward and away from each other (See FIG. 8). Pivot pins 60 are provided on the far end of the L-shaped arms 45 and are adapted to rotatably seat into the locating apertures 61 provided in the base 36, thereby fixing the free ends of the L-shaped arms with respect to the base 36, and as a result the housing. The free ends of the L-shaped arms 45 pivot about the pins 60, seated in aperture 61. A pair of locator walls 62 extend perpendicularly from the base 36 and are provided with semi-circular groves 63 which act as bearing surfaces and allow for the smooth rotation of the pivot pins 60.

The piston rod 18 extends through the threaded passageway 64 provided in the split-nut 51 and through the unthreaded passageway 65 provided in base 36.

Figure 6:
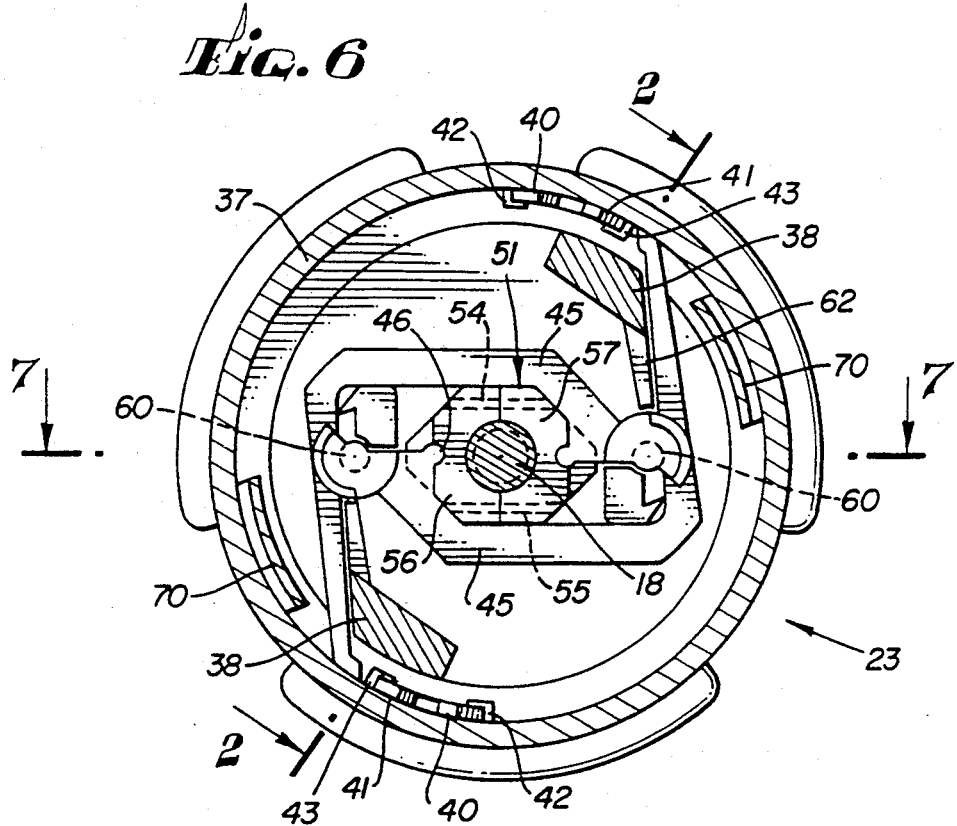
FIG. 6 is a transverse cross-sectional view taken along the lines of 6—6 shown in FIG. 2 and 7
Figure 7:
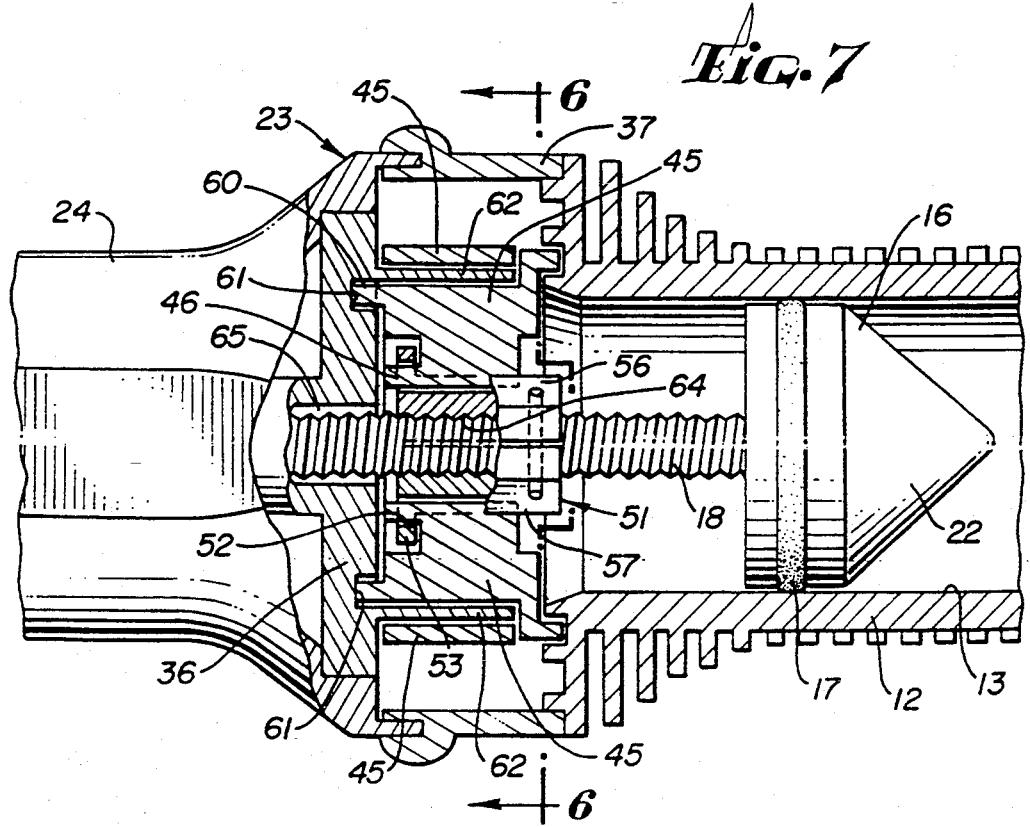
FIG. 7 is a partial longitudinal view taken along the lines of 7—7 shown in FIG. 6.

The operation of the mode selector switch 23 is best illustrated in the sequence of FIGS. 6, 7, 8, 9 and 10. FIGS. 6 and 7 show the relative positions of the various components in the first position wherein the split-nut halves 56 and 57 are threadably engaged with the threads on piston rod 18 to prevent the longitudinal movement of the piston 16 except by the rotational movement of the piston rod 18. In this position the pivot pins 60 prevent the outward movement of the split nut halves 56 and 57 so that when there is high fluid pressure acting on the front 22 of the piston 16 and this high pressure is translated into a separating force (through the threads) on the split nut halves, there is no tendency for the halves to separate.

Rotation of the selector sleeve 37 or the extension 24 from the first position shown in FIG. 6 to the second position shown in FIG. 8 rotates the free ends of the L-shaped arms 45 which are pivotally fixed to the base 36 outwardly so as to generate a spring force which urges the mechanism 38 to return to the first position and to separate the split-nut halves 56 and 57 sufficiently to disengage of the threaded passageway 64 from the threaded section of the piston rod 18. Without this threaded connection, the piston 16 is free to move longitudinally through the bore by pushing or pulling on the handle 21 thereon. The extension 24 on the operation mode selector cap 23 in conjunction with the overhanging handle 21 as seen in FIG. 2 allows the cap 23 to be changed from position to position while the operator is holding onto the handle 21, notwithstanding the position of the handle.

With reference to FIGS. 5 and 10, position holding members 70 are secured by one end thereof to the edge of the selector sleeve 37 in opposing positions. The depending free end 71 slide along the inner edge of the ridges 72 provided on the open end 14 of the housing 12. The more inwardly projecting section 73 of the ridge 72 is provided with slight tapers at each end thereof toward adjacent sections of the ridge to guide the position holding members 74 and 75. As the selector sleeve 37 is rotated from one position to the other, the position holding members 70 move along the edge of the more inwardly projecting section 73 of the ridge. At the ends thereof the position holding members 74 and 75 slide into the adjacent sections and thereby hold the selector switch 23 in the first position on one side of section 73 and in the second position on the other side and provides the snap fit sensed by the operator when turning the selector sleeve 37.

A typical operation of the inflation device is as follows: The valve body 35 in valve 32 is positioned so that radiopaque inflation fluid can be drawn into the bore 13 of the inflation device 10 from a container by pulling on the piston rod handle 21. When the desired amount of inflation fluid is drawn into the bore 13, the valve body 35 is rotated to connect the interior bore 13 with the proximal end of the dilatation catheter 66 and then the piston rod handle is pushed to inject the inflation fluid into the dilatation catheter to inflate the balloon. This procedure is employed to prime the catheter and remove any air therefrom before the catheter is inserted into the patient as well as to initially fill the catheter prior to inflating the balloon after the catheter is inserted into the patient. A vacuum can be generated by pulling on the handle 21 to remove inflation fluid from the catheter to deflate the balloon 66. For this procedure the operation mode selector switch 23 is in the second position wherein the split-nut halves 56 and 57 are spaced from the piston rod 18 so there is no threaded engagement therebetween. During the final inflation of the balloon for dilatation of the stenosis, the first position is preferred in order to have better control thereof. In this instance either the selector sleeve 37 or the extension 24 is manipulated by the fingers of the hand engaging the handle 21 to change the position thereof by the rotation of the sleeve or extension so that the split-nut halves 56 and 57 engage the threaded portion of piston rod 18. With the first position established, the handle 21 can be rotated clockwise until the desired amount of inflation liquid has been injected into the dilatation catheter 11 or the maximum pressure is reached. This position can also be used to lock the position of the piston under either pressure or vacuum.

Usually, the inflation of the balloon 66 is monitored fluoroscopically by the physician to ensure that the balloon reaches its desired cylindrical shape while simultaneously observing the pressure display 31 to ensure that excessive pressures are not developed within the balloon. When the dilatation of the stenosis is complete, the selector sleeve 37 or the extension 24 is rotated to put the operation mode selector switch 23 back into the second position so that the balloon can be rapidly deflated by pulling on the handle 21.

The various components of the present inflation device can be made from conventional materials and a wide variety of metals and plastic resins may be employed for this purpose. The embodiment shown in the drawings and described herein was designed to be made of plastic materials except for the piston rod, the pressure sensor and the display. Polycarbonate resins such as Makrolon resin which is available from MOBAY Chemical Corp. are presently preferred for the plastic parts except for the split collar or a nut which is preferably formed of a nylon (e.g. Nylon 66) because of the strength and lubricous nature of this material. The piston rod is preferably made of stainless steel.

As shown in the drawings, the exterior of the housing 12 is provided with a ribbed structure which greatly facilitates the gripping of the housing by the physician even when the physician's glove may be covered with various fluids during the period when the inflation device is being used. Other means to facilitate the gripping of the device may of course be employed.

FIG. 11 illustrates an alternate embodiment of a split-nut 80 suitable for use in the inflation device of the invention. In this embodiment the split-nut section 81 is provided with a pair of arms 82 which slide along the channel or grooves 73 provided in the other split-nut section 84 to maintain their orientation as they move toward and away from one another.

The invention has been described herein primarily directed to certain preferred embodiments, but those skilled in the art will recognize that modifications can be made thereto. For example, the angled spring members are described and shown herein as having relatively straight sections. However, curved sections or combinations of curved and straight sections may be used. Other modifications and improvements can be made without departing from the scope of the invention.

What is claimed is:

1. A fluid injecting device comprising;
   (a) an elongated housing having an inner bore extending therein;
   (b) a piston slidably disposed within the bore of the housing;
   (c) an elongated piston rod having one end secured to the piston and one end extending out of the housing and an intermediate section with threads on the exterior thereof;

(d) a plurality of opposed threaded members adapted to engage the threaded section of the piston with each of said threaded members being secured to an arm;

(e) means to move the arms to which the threaded members are secured so as to move the opposed threaded members to a first position with the threads thereon engaged with the threads on the piston rod so that longitudinal movement of the piston within the bore is effected by rotating the piston rod; and (f) means to move the arms to which the threaded members are secured to move the opposed threaded members to a second position spaced away from the piston rod with the threads thereon disengaged from the threads on the piston rod, so that longitudinal movement of the piston within the bore is capable of being effected by pushing or pulling on the piston rod.

2. The fluid injecting device of claim 1 wherein the arms are secured to a positioning switch mounted on the open end of the housing.

3. The fluid injecting device of claim 2 wherein the positioning switch is operated by a cylindrically-shaped sleeve rotatably mounted on the open end of the housing coaxially with the piston rod.

4. The fluid injecting device of claim 3 wherein the rotatably mounted sleeve is provided with an extension fixed thereto so that the switch can be operated by rotating the sleeve or the extension connected thereto with the fingers of an operator's hand engaging a handle on the end of the piston rod extending out of the housing.

5. The inflation device of claim 2 wherein the opposed threaded members include a split nut having two sections with guide means to maintain the alignment of the section as they move toward and away from each other.

6. The inflation device of claim 5 wherein the arms are angled spring members having one end fixed to the rotatable sleeve and one end pivotally fixed to a base secured to the housing.

7. The inflation device of claim 6 wherein the sections of the split nut are rotatably mounted to the angled spring member adjacent to the ends pivotally mounted to the base.

8. The inflation device of claim 3 wherein the sleeve which is rotatably mounted onto the open end of the housing has opposed guide fingers secured to the inner surface thereof which have free ends adapted to follow arcuate ridges provided in the edge of the open end of the housing.

9. The inflation device of claim 8 wherein the arcuate ridges have central sections with a smaller radii of curvature than adjacent sections.

10. The inflation device of claim 6 wherein the end of the angled spring members pivotally mounted to the base are provided with a pivoting post, one end of which is seated in an aperture in the base and the other end of which is seated in a recess provided in the open end of the housing.

11. The inflation device of claim 6 wherein the angled spring members are generally L-shaped.

12. The inflation device of claim 11 wherein the L-shaped angled spring members are fixed at one end thereof to opposed locations within the sleeve and extend inwardly beyond the center thereof.

13. The inflation device of claim 7 wherein each of the split nut sections is provided with a groove on the backside thereof with a flange having an aperture therein extending out from one end thereof.

14. The inflation device of claim 13 wherein each of the angled spring members are provided with a post adjacent to the pivoted end thereof which is seated within the groove end and which has an extension seated within the aperture provided in the flange.

15. The inflation device of claim 4 wherein the handle secured to the piston rod is generally cup shaped and extends toward the housing exterior to the sleeve extension.

16. A fluid injecting device comprising:
(a) an elongated housing having an inner bore extending therein;
(b) a piston slidably disposed within the bore of the housing;
(c) an elongated piston rod having one end secured to the piston and one end extending out of the housing and an intermediate section with threads on the exterior thereof;
(d) a split nut having two sections with corresponding opposed threaded members adapted to engage the threaded section of the piston and guide means to maintain the alignment of the sections as they move toward and away from each other;
(e) means to move the opposed threaded members to a first position with the threads thereon engaged with the threads on the piston rod so that longitudinal movement of the piston within the bore is effected by rotating the piston rod;
(f) means to move the opposed threaded members to a second position spaced away from the piston rod with the threads thereon disengaged from the threads on the piston rod, so that longitudinal movement of the piston within the bore is effected by pushing or pulling on the piston rod; and
(g) the means to move the threaded members toward and away from the threaded piston rod including a positioning switch mounted on the open end of the housing for actuating said split nut to move said threaded members toward and away from the piston rod.

17. A fluid injecting device comprising:
(a) an elongated housing having an inner bore extending therein;
(b) a piston slidably disposed within the bore of the housing;
(c) an elongated piston rod having one end secured to the piston and one end extending out of the housing and an intermediate section with threads on the exterior thereof;
(d) a plurality of opposed threaded members adapted to engage the threaded section of the piston;
(e) means to move the opposed threaded members to a first position with the threads thereon engaged with the threads on the piston rod so that longitudinal movement of the piston within the bore is effected by rotating the piston rod;
(f) means to move the opposed threaded members to a second position spaced away from the piston rod with the threads thereon disengaged from the threads on the piston rod, so that longitudinal movement of the piston within the bore is effected by pushing or pulling on the piston rod;

(g) the means to move the threaded members toward and away from the threaded piston rod including a positioning switch mounted on the open end of the housing, the positioning switch including a cylindrically-shaped sleeve rotatably mounted on the open end of the housing coaxially with the piston rod and having opposed guide fingers secured to the inner surface thereof which have free ends adapted to follow arcuate ridges provided in the edge of the open end of the housing.

* * * * *